United States Patent [19]

Djerassi

[11] 4,111,199

[45] Sep. 5, 1978

[54] METHOD OF COLLECTING TRANSFUSABLE GRANULOCYTES BY GRAVITY LEUKOPHERESIS

[76] Inventor: Isaac Djerassi, 2034 Delancey Pl., Philadelphia, Pa. 19103

[21] Appl. No.: 783,380

[22] Filed: Mar. 31, 1977

[51] Int. Cl.$^2$ .............................................. A61M 5/00
[52] U.S. Cl. ................................ 128/214 R; 23/230 B
[58] Field of Search ............... 128/214 R, 213, 214 B, 128/2; 23/230 B

[56] References Cited

U.S. PATENT DOCUMENTS

| | | | |
|---|---|---|---|
| 3,489,145 | 1/1970 | Judson et al. | 128/214 R |
| 3,892,236 | 7/1975 | Djerassi | 128/214 R |

OTHER PUBLICATIONS

A. J. Roy et al., "A Method for Separation of Granulocytes from Normal Blood Using Hydroxyethyl Starch," Preparative Biochemistry, vol. 1, No. 3, pp. 197-203 (1971).
Chaplin et al., "Methods for Preparation of Suspensions of Buffy Coat-Poor Red Cells for Transfusion," American Journal of Clinical Pathology, vol. 31, No. 5, pp. 373-383 (1959).

Primary Examiner—Stephen C. Pellegrino
Attorney, Agent, or Firm—Caesar, Rivise, Bernstein & Cohen, Ltd.

[57] ABSTRACT

A leukopheresis process comprising removing a quantity of whole blood from the vein of a donor and depositing the blood in a plastic blood collection bag. The bag is then centrifuged in order to separate the red and white cells from the supernatant plasma and platelets. The platelet rich plasma is then expressed from the bag into a satellite bag. A solution comprising a red cell sedimenting agent in Normal Saline is then introduced into the bag containing the red and white cells. Preferably, the sedimenting agent is hydroxyethyl starch. After a short period of time, the red cells sediment to the bottom of the plastic bag, with the white cells, sedimenting agent and Saline remaining as the supernatant. The red cells are then removed from the bag, mixed with the platelet poor plasma, which is obtained by centrifuging the platelet rich plasma and removing the platelets, and the red cells and platelet poor plasma are returned to the donor by infusion into a vein. The white cells are removed from the Normal Saline and sedimenting agent solution by gravity or centrifugation, and are administered to a donee requiring granulocyte transfusions.

17 Claims, 8 Drawing Figures

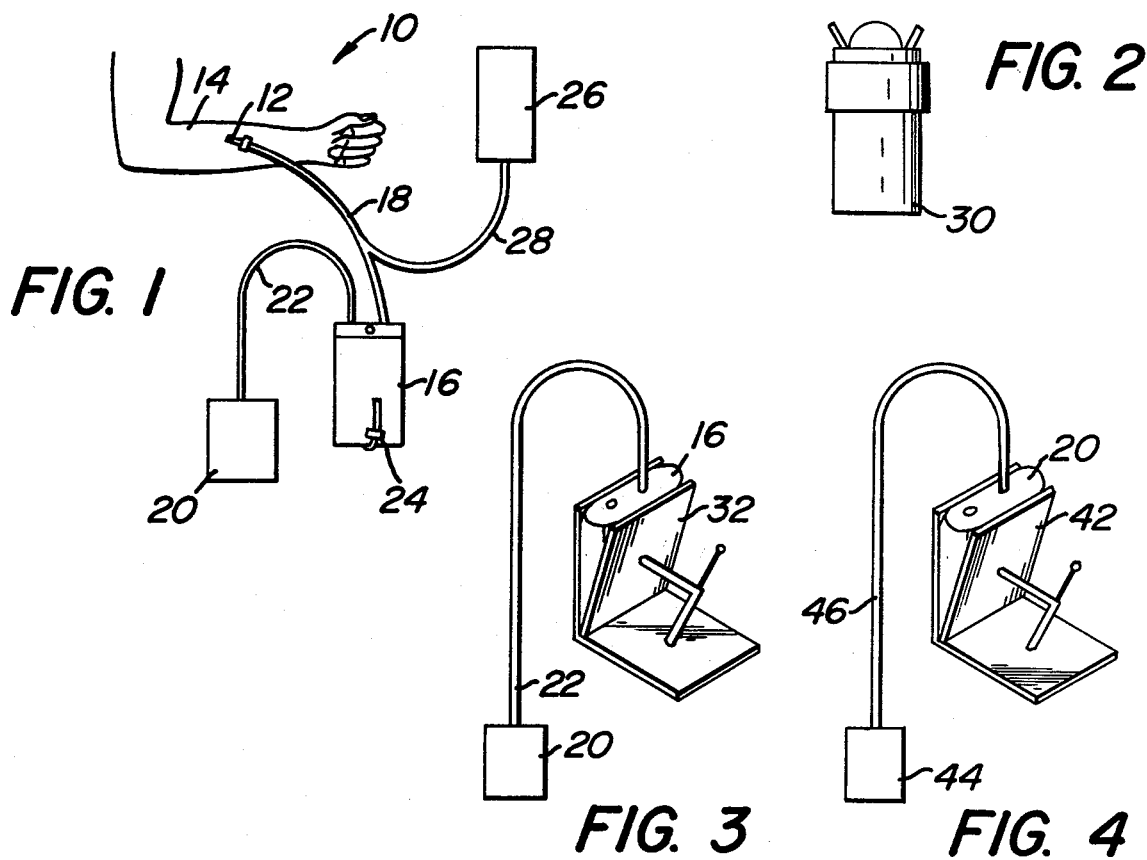
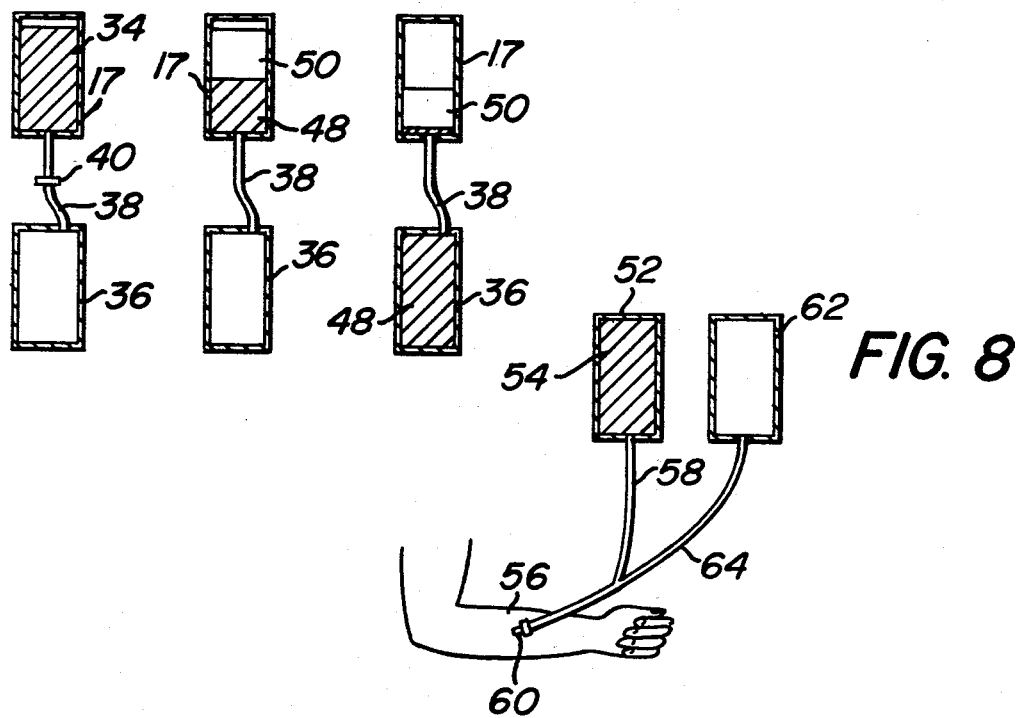

METHOD OF COLLECTING TRANSFUSABLE GRANULOCYTES BY GRAVITY LEUKOPHERESIS

This invention relates to a leukopheresis process for obtaining granulocytes for transfusion and, more particularly, to a leukopheresis process that utilizes gravity sedimentation to remove red cells from the white cells which are to be injected.

Human blood comprises red cells (erythrocytes) and white cells (leukocytes). The leukocytes in turn consist of monocytes, lymphocytes and granulocytes. The granulocytes comprise approximately 70 to 80% of the leukocytes. The granulocytes are involved in various defense and repair functions. They are the first cells to appear at a sight of inflammation. Their function is to fight bacterial infection of a human being.

Granulocytes are now transfused into patients for various purposes. They are used where therapy with appropriate antibiotics has failed to control an infection in the granulocytopenic patient. They are used in the treatment of patients with acute or chronic leukemia, aplastic anemia or bone marrow transplant recipients.

The use of transfusions of human granulocytes to infected leukopenic patients commenced about 20 years ago. The original method of obtaining granulocytes was to remove a small quantity of blood, such as a pint (473 ml), into a plastic bag and centrifuge the bag in order to remove the plasma and platelets. The remaining red and white cells were then permitted to rest in the bag and the red cells would sediment and the white cells would remain as a buffy coat above the red cells. The red cells could then be withdrawn and the granulocytes and other white cells could be recovered from the buffy coat. These granulocytes were then injected into the donee or patient.

One of the problems with this type of separation is that a given donor could only provide small quantities of white cells in any given time period since the donor can only donate 1 pint (473 ml) of whole blood every 8 weeks. This problem was overcome by the advent of leukopheresis. Utilizing leukopheresis, large quantities of white cells could be obtained in a given day from the donor. In the leukopheresis process, blood is continuously withdrawn from the donor, the white cells are removed from the blood and the red cells and plasma, and most of the platelets, are reinjected into the donor. In a leukopheresis procedure on a donor, as many as 24 pints (473 ml each) can be processed. This allows collection of very large numbers of granulocytes from a single donor.

Up until this invention, leukophereses were conducted by either continuous or interrupted flow centrifugation or filtration leukopheresis. A description of all of these methods and the use of the recovered granulocytes can be found in a publication entitled "Leukopheresis And Granulocyte Transfusions," published by American Association of Blood Banks, Washington, D.C., in 1975. Apparatus for carrying out the continuous flow centrifugation leukopheresis can be found in U.S. Pat. Nos. 3,489,145 and 3,655,123. Apparatus for carrying out filtration leukopheresis can be found in applicant's prior U.S. Pat. Nos. 3,802,432 and 3,892,236. Both the continuous flow centrifugation and filtration leukopheresis are based on establishing a vein-to-vein extracorporeal blood circulation and extracting continuously the granulocytes from recirculated blood.

The efficiency of centrifugation for separating normal human granulocytes was increased by adding a high molecular weight material, namely, hydroxyethyl starch, to the blood prior to or during the centrifugation. This procedure was based on applicant's prior discovery that this material is very effective and superior to other similar materials for separation of granulocytes from red cells by simple gravity sedimentation, unassisted by centrifugation. The ability of large molecular weight materials to facilitate the separation of white blood cells from red cells has been known for some time. High molecular weight dextran has been used for the collection of laboratory amounts of white cells for some twenty years. Among the high molecular weight materials used for these purposes were polyvinylpyrrolidone, dextran or hydroxyethyl starch (HES). The effect of these materials is based on the fact that such materials cause reversible aggregation of red cells, which then sediment faster then singular granulocytes in an aqueous medium. The mechanism for this faster sedimentation is not clearly understood. However, it is believed that the large molecular weight materials cause an increase of the so-called sedimentation rate of the blood. Since the sedimentation rate of blood is also increased by natural products found in the blood, such as fibrinogen, addition of pure fibrinogen could also be used for separation of granulocytes from red cells. In fact, all large molecules, synthetic or natural, capable of increasing the sedimentation rate of blood would produce the same result.

Separation of blood into elements can therefore be achieved by simple gravity, or in other words, letting blood with an anticoagulant stand in an appropriate container without being disturbed for a period of time.

Under these conditions the red cells would settle at the bottom of the container, being the heaviest, with the white cells concentrating in the upper layers of the red cells and just above them, to form the so called buffy coat. The plasma with the platelets floats above the red cells and the buffy coat. The separation of these elements into separate containers can be achieved by aspiration of each layer or by squeezing the original container, if flexible, and expulsing the portions of the contents as they come up to a suitably located opening. The latter process is the basis for the separation of blood components using plastic bags and centrifugation. The speed of separation of the blood elements by gravity is not practical for pheresis procedures because of the many hours required for sedimentation of the elements in whole blood and an anticoagulant (ACD), without additives.

Such separation is greatly increased by the addition to the blood of materials which increase the sedimentation rate, such as high molecular weight dextran, HES, fibrinogen, polyvinylpyrrolidone, and many other materials generally referred to as plasma expanders or red blood cell sedimenting agents.

The addition of such materials, and particularly HES, is necessary for efficient separation of granulocytes from the red cells of human blood, even when the blood is centrifuged. By adding HES to the donor's blood the efficiency of the continuous flow centrifuges or the discontinuous flow centrifuges has been increased from 5% to about 20% and 40%, respectively. This use of HES in fact made these centrifuges more practical, even though not ideal, for harvesting normal human granulocytes for transfusion.

Up until the advent of the instant invention, as pointed out above, collection of human granulocytes in amounts suitable for transfusion has been accomplished only by methods of pheresis with centrifugation, with or without HES or other high molecular weight materials, or by filtration. Prior to the instant invention, sedimentation unassisted by centrifugation for the separation of white cells has not been used for collection of granulocytes to be transfused, nor has it been used in a pheresis process.

The method of this invention is a leukopheresis process in which the granulocytes are harvested by simple gravity in sufficient amounts for transfusion.

It is accordingly an object of this invention to provide a novel method of collecting transfusable granulocytes.

It is a further object of this invention to provide a method of collecting granulocytes by gravity leukopheresis.

These and other objects of this invention are accomplished by providing a method comprising withdrawing a portion of blood from a human blood donor, separating the red and white cells from the plasma and platelets in the blood, mixing the red and white cells with a solution comprising a red blood cell sedimenting agent and Normal Saline, permitting the mixture to stand to permit the red blood cells to sediment to the bottom of the container in which the mixture is placed, removing the red blood cells by gravity, separating the white cells from the solution for subsequent transfusion to a patient, mixing the red cells with the previously removed plasma, and reinjecting the red cells and plasma into the white cell donor.

Other objects and many of the attendant advantages of this invention will be readily appreciated as the same becomes better understood by reference to the following detailed description when considered in connection with the accompanying drawings wherein:

FIG. 1 is a schematic view showing the collection of the blood from a donor;

FIG. 2 is a schematic view showing the step of centrifuging the collected blood;

FIG. 3 is a schematic view showing the separation of the platelets and plasma from the red and white cells;

FIG. 4 is a schematic view showing the separation of the platelets from the plasma;

FIG. 5 is a schematic view showing the red and white cells in solution with HES and Saline, prior to sedimentation;

FIG. 6 is a schematic view showing the sedimented red cells prior to draining;

FIG. 7 is a schematic view showing the drained red cells; and

FIG. 8 is a schematic view showing the return of the red cells and platelet poor plasma to the donor.

Referring now in greater detail to the various figures of the drawings wherein like reference characters refer to like parts, the first step in carrying out the process of this invention is generally shown at 10 in FIG. 1. As seen in FIG. 1, a metal needle or venous plastic catheter 12 is inserted in a large vein in the donor's arm 14. The donor can be any normal healthy individual eligible for donating whole blood according to American Red Cross and American Association of Blood Banks standards. One pint (473 ml) of blood is collected in a 600ml plastic bag 16 which contains 75ml ACD (formula A) as an anticoagulant, or any equivalent calcium binding anticoagulant. The blood is collected through flexible tube 18. A satellite bag 20 is connected to bag 16 by a flexible transfer tube 22. A roller clamp 24 releasably seals the bag 16 containing the blood.

When bag 16 is filled with 1 pint (473 ml) of blood, the bag 16 and its satellite bag 20 are removed, and the bottom of tube 18 adjacent the top of bag 16 is temporarily closed. With the bag 16 removed, Normal Saline solution is administered to the donor from plastic bag 26 through tube 28 and into tube 18. The purpose of the Normal Saline is to keep the needle in the donor's vein open when blood is not being withdrawn.

Bag 16, containing the blood, and its satellite bag 20 are then placed in a centrifuge 30, where the bag and its contents are centrifuged at room temperature as long as needed to sediment the red blood cells and the white blood cells. Centrifugation for 6 minutes at 2000 rpm is adequate when a Model PR-6 International centrifuge is used. The centrifugation separates the contents of the bag into red cells, which are lowermost, a buffy coat, which contains the white cells, and the platelets and plasma, which are uppermost. Bag 16 is then placed in a conventional bag press 32, with the red cells being lowermost.

The bag press 32 is then used to exert pressure on the flexible bag 16, and this forces the plasma and platelets through transfer tube 22 into bag 20. Transfer tube 22 is then disconnected from bag 16.

HES (3%) in Normal Saline (0.9% sodium chloride in distilled water) is then added to the packed red cells and white cells to achieve an approximate hematocrit of 30%. Alternately, 500ml of 3% HES in Normal Saline can be added without regard for the hematocrit. The red cells and white cells are mixed thoroughly with the HES solution in an 800ml plastic bag 17, which is then hung with the outlets pointing down, as shown in FIG. 5. As seen in FIG. 5, the HES solution with the red and white cells is schematically shown at 34. A transfer bag 36 is attached to bag 17 by a transfer tube 38. The tube 38 is closed by a roller clamp 40.

The bag 17 is hung in an immobile condition, and the red cells are permitted to sediment. After the red cells are sedimented, but prior to the formation of a heavy buffy coat, the roller clamp 40 is removed and the red cells are drained into the transfer bag 36. This leaves between 10 and 20ml of red cells in the original container 17, together with the supernatant consisting of white blood cells and the HES solution. The time for separation of the red cells by gravity is approximately 12 to 20 minutes, depending on the size of the bag 17, as will be explained hereinafter.

During the time that the red blood cells are sedimenting, and are subsequently drained, the bag 20 containing the platelet rich plasma is centrifuged at 2800 rpm for ten minutes in a Model PR-6 International centrifuge or a similar apparatus. This separates the platelets from the plasma, and the platelets are in the lower part of the bag. The bag 20 containing the platelet and plasma portions is then placed in a bag press 42, and compressed. The upper platelet poor plasma portion is transferred into a flexible plastic bag 44 by transfer tube 46.

Referring now to FIG. 6, the red blood cells are shown at 48 and the white cells and HES solution are shown at 50 in upper bag 17, just prior to draining of the red cells 48. The drained red cells are shown at 48 in FIG. 7, with the white cells and HES solution, plus a small amount of red cells remaining in the upper bag 17.

The sedimented red cells 48 are then combined with the platelet poor plasma in bag 44, and the combination is placed in plastic bag 52. The combination of the sedimented red cells and platelet poor plasma is shown at 54 in FIG. 8.

The plasma and red cells are preferably reinfused into the other arm 56 of the donor through the use of plastic tubing 58 and a second venous catheter 60 inserted in the arm. A bag 62 containing Normal Saline is connected by tube 64 to catheter 60. The Normal Saline is used to keep the needle in the vein in arm 56 open when no blood and plasma are being reinfused into the donor.

While returning the plasma and the red cells to the donor, a second pint (473 ml) of blood is collected in another 600ml plastic bag containing ACD anticoagulant. The plastic bags containing the supernatant HES solution are centrifuged immediately after draining the sedimented red cells at 2800 rpm for 10 minutes. The supernatant HES sulution is removed by a bag press and discarded, leaving some red cells and the leukocytes in the bag. About 50ml of normal ABO compatible plasma is introduced into this bag and the cells are resuspended by gentle shaking. The procedure is repeated as many times as the donors wish to stay.

At the end of the procedure the contents of all of the bags with leukocytes are pooled. The red cells can be sedimented again by addition of 6% HES in Normal Saline in a ratio sufficient to produce a final concentration of 1 to 3% of HES. The red cells (up to 100ml) are drained again and can be returned to the donor, leaving mainly leukocytes and some platelets in the final concentrate.

The procedure is greatly accelerated in large donors who can tolerate well the consecutive collection of two pints (473 ml each) of blood in two separate ACD containing bags. In such cases the two pints (473 ml each) of blood are processed separately, but simultaneously, as described above. Bleeding of the donor is resumed after at least 1 pint (473 ml) of plasma plus red cells has been returned to the donor. In these latter donors, 3 pints (473ml each) of blood can comfortably be processed and the leukocytes pheresed in about 3 to 3½ hours. When smaller sized donors are only available, 1 pint (473ml) of blood can be collected 1 day prior to leukocyte donation, and is then returned to the donor while collecting 2 pints (473ml each) from simultaneous extraction of leukocytes. Should the donor plan to return for a repeated donation within a few days, the last pint (473ml) of blood collected is stored unprocessed at 4° C. for priming on the next leukocyte donation. Alternatively, when leukocyte donation is needed without prior notice and the donor is of small size, pheresis of leukocytes is carried out from 1 pint (473ml) of blood at the time, and then retaining unprocessed the last pint (473ml) collected for use as a priming blood on the following donation. The latter can then be carried out with simultaneous processing of 2 pints (473ml each) of blood.

Steroids, such as 200mg hydrocortisone, can be given to the donors at the start of the procedure in order to induce some leukocytosis during the latter part of the procedure.

Donors tolerate this procedure well. The only type of reaction which may occur is the reaction typical of whole blood donation. The yield of granulocytes averages $1.7 \times 10^{10}$ when 6 pints (473ml each) of blood are processed. Differential counts carried out on the final leukocyte concentrates show that 92 to 95% of the cells are granulocytes. Study of the granulocytes obtained by the process of this invention showed well preserved morphology, 99% exclusion of trypan blue and pseudo formation and good motility under phase microscopy. Over 80% of the cells can phagocytize. Bacteriological studies carried out on multiple leukocyte conentrates failed to reveal bacterial contamination.

As pointed out above, the time required to sediment the red blood cells in bag 17 is dependent on the width of the bag. Time tests were conducted in order to determine the amount of time to sediment the red blood cells taken from 1 pint (473ml) of whole blood and suspended in 500ml of 3% HES in Normal Saline. Three different types of bags with different width were used in the tests. The following chart shows the time in minutes required for sedimentation with each of the bags:

| TEST NO. | 4¾ INCH (12.1 cm) WIDTH BAG | 8¾ INCH (22.2 cm) WIDTH BAG | 10½ INCH (26.7 cm) WIDTH BAG |
|---|---|---|---|
| 1 | 18 | 13 | 12 |
| 2 | 20 | 14 | 12 |
| 3 | 19 | 14 | 10.5 |
| 4 | 17 | 15 | 9 |

In the foregoing chart, all times are expressed in minutes. As is apparent, the wider the bag used, the shorter the time required to obtain the sedimentation of the red blood cells necessary to carry out the process of this invention.

Another series of tests was conducted in order to determine the time required for red cell sedimentation, in minutes, with varying percentages of HES. In these tests, red cells packed together by centrifugation and relatively devoid of plasma were resuspended in HES solution in Normal Saline, at a constant hematocrit of 30%. The time required for sedimentation of the red cells was determined at 1% increments of HES, commencing with 1% and ending with 6%. These tests gave the following results:

| PERCENTAGE HES | TIME REQUIRED FOR RED CELL SEDIMENTATION IN MINUTES |
|---|---|
| 1% | 30 plus |
| 2% | 20 |
| 3% | 12 |
| 4% | 15 |
| 5% | 17 |
| 6% | 21 |

It is thus seen from the foregoing tests that the minimal time required, and thus the optimum result, was 12 minutes when a 3% solution of HES was used.

The method of this invention provides a simple method for leukopheresis. It differs from all leukopheresis techniques previously conceived and used. All previous methods for pheresis utilize centrifugal force or selective filtration to separate and harvest leukocytes. The new method utilizes only gravity, unassisted by simultaneous centrifugation, to separate the white cells from the red cells. The acceleration of the separation of granulocytes by a macromolecular agent, such as HES, in low viscosity saline, makes the use of the agent practical for pheresis of large blood volumes. The use of the low viscosity saline, or its equivalent, with HES is critical to the invention. WIthout this solution, the time required for granulocyte separation by gravity is impractical for large volume recovery of granulocytes by pheresis.

Prior to this invention, it was suggested in the art that red blood cell sedimenting agents or plasma expanders, such as HES, dextran, polyvinylpyrrolidone or fibrinogen, could be used in gravity sedimentation to separate red cells from white cells. In all of these reports, however, the solution of the sedimenting agent was added first to the whole blood without removing the plasma. As a result, the time needed for sedimenting the red blood cells was unduly prolonged. This process would therefore not be desirable for leukopheresis, which is limited by the time the donor has available. In this connection, note "A Method for Separation of Granulocytes From Normal Human Blood Using Hydroxyethyl Starch" appearing in Volume 1, No. 3 of Preparative Biochemsitry, pages 197–203 (1971), by A. J. Roy et al. Applicant herein was one of the co-authors of this article.

The article discusses work which was carried out to determine whether the addition of red blood cell sedimenting agents, especially HES and dextran, could be used for separating red cells from white cells. HES and dextran were added to red and white cells in plasma in order to give final concentrations of HES or dextran ranging between 2 and 4%. The hematocrit, which originally ranged between 45 and 50% was adjusted, if necessary, to 30% by the addition of autologous plasma.

The tests showed good granulocyte recovery. However, the sedimentation time for the red blood cells ranged between 54.2 and 82.9 minutes.

Similarly, note "Methods for Preparation of Suspensions of Buffy Coat - Poor Red Blood Cells for Transfusion," appearing in Volume 31, No. 5, of American Journal of Clinical Pathology, pages 373 to 383 (1959) by Chaplin et al, in which dextran was added to whole blood in order to free the red cells of white cells.

Although these prior tests with dextran and HES did prove that these materials could be used for separating red blood cells from white blood cells, the times involved were far too long to enable these materials to be used in leukopheresis.

One of the key features of the instant invention is the realization that sedimentation rates for red cells could be greatly increased by utilizing the low viscosity Normal Saline as a diluent of the red cells in the absence of plasma. In the aforementioned Roy et al article, and in the first step of the process in Chaplin et al, the plasma was not removed, which resulted in the extremely long sedimentation times.

Although the invention has been disclosed principly utilizing HES as the red blood cell sedimenting agent, it is to be understood that other red blood cell sedimenting agents can also be used. Thus, the invention can be carried out by utilizing polyvinylpyrrolidone, dextran or fibrinogen. However, HES is the preferred material, being the most rapid to act, and since there are minor handicaps connected with the use of the other agents. Polyvinylpyrrolidone is cleared from the recipient's body very slowly and possibly not completely after infusion, and thus is not desirable for clinical use. Dextran preparations are potentially antigenic, and adversely affect the clotting mechanisms. Fibrinogen obtained from pooled human plasma increases the risk of transmitting hepatitis.

On the other hand, HES is eliminated well from the body after infusion, has not been associated with allergic reactions in experimental animals or in man, and does not augment the risk of hepatitis. These factors, added to the technical advantages illustrated by the results of the present experiments, point to HES as the sedimenting agent of choice in the production of granulocytes in leukopheresis.

Although Normal Saline has been disclosed as the diluent for the HES in this invention, it is to be understood that other isotonic balanced salt solutions, which may be buffered, can be used in place of Normal Saline. Among the other solutions that can be used are Ringer's solution or Ringer's lactate solution.

The collected granulocytes produced by the method of this invention are normally injected in the patient within twenty-four hours after their production, in the same manner as is done in connection with the recovery of granulocytes through the continuous flow centrifugation or filtration leukophereses presently being carried out.

The process of this invention possesses many advantages over all known leukophereses presently being employed. The efficiency of granulocyte separation by the method of this invention is far superior to that of the continuous flow centrifugation or interrupted flow centrifugation of blood, even when HES is used in the centriguation. Thus, the instant invention obtains 80% recovery of the granulocytes versus 20% recovery in the continuous centrifugation method utilizing HES. Although the procedure of this invention can be carried out by the addition of HES to whole blood, as is done in the centrifugation techniques, the time required for separation of the granulocytes is substantially longer than when the packed red and white cells are suspended in the HES-Saline solution. The lesser viscosity of the HES-Saline, as compared to HES-plasma, is most likely responsible for the crucial acceleration.

Accordingly, the yield of granulocytes collected by the process of this invention per unit of time is equal to or superior to pheresis by continuous flow contrifugation. However, utilizing the process of this invention, the safety of the donor is absolute, since he is not attached to any mechanical and power devices for withdrawing, propelling and reinfusing the blood, as occurs with the use of continuous or interrupted flow centrifugation.

The volume of blood processed by this invention is four times smaller than the volume of blood which is processed and mildly traumatized in the continuous flow centrifugation pheresis. To obtain by centrifugation the number of cells provided by 6 pints (473ml each) of blood using the process of this invention would require the withdrawing, centrifuging, propelling and pressure reinfusion of 24 pints (473ml each) of blood in the continuous centrifugation process, or at least 12 pints (473ml each) in the interrupted flow centrifugation process. Additionally, the pumps used for the centrifugation process have been shown to damage the blood.

The process of this invention does not require heparinization of the donor, which is needed in filtration leukopheresis, and in many of the centrifugation procedures. The cells obtained by the process of this invention do not come in contact with a foreign surface capable of activating them, as occurs in filtration leukopheresis, which requires nylon filters.

The safety of the process of this invention is comparable to that of traditional single pint (473ml) collection of blood or ordinary plastic bag platelet pheresis. It can be carried out in all ordinary blood banks by semiskilled personnel without requiring continuous supervision by trained physicians, as are needed for the previously described leukophersis methods of filtration or centrifugation.

Both centrifugation leukopheresis and filtration leukopheresis require expensive equipment, which can cost as much as $42,000.00. The carrying out of the process of this invention does not require the large initial investment needed for the other phereses. Additionally, there are no problems connected with maintenance of such apparatus. There are no opportunities for malfunction of complicated mechanical devices utilizing the process of this invention. These mechanical devices, if they malfunction, can harm the donor and may prevent the collection and supply of granulocytes to critically ill patients needing the lifesaving granulocytes.

A leukopheresis laboratory using the process of this invention can process simultaneously as many donors as necessary to supply all patients. This is impossible with the previous techniques, because of the cost and logistics of storing many extremely expensive machines for occasional simultaneous use.

The collection of normal granulocytes by the process of this invention is in all respects comparable to the traditional plasma phereses and platelet phereses. In view of the widespread capability to carry out these latter procedures at practically any hospital, granulocyte transfusions may now become as routine as platelet transfusions. Insofar as the platelet transfusions are concerned, the platelets separated by the process of this invention can be used in any known procedure for platelet transfusion. A summary of the use of these platelets can be found in "Control And Prevention of Hemorrhage: Platelet Separation," Klein et al, Cancer Research, Volume 25, No. 9, pages 1504–1509 (1965). The Applicant herein is a co-author of this article.

The percentage by weight of HES in the Normal Saline can very over a relatively wide range. As shown in the chart above, good results can be obtained utilizing a percentage of between 1½% HES and 6% HES. The best results are obtained when utilizing 3% HES. Similar results can be obtained using like amounts of the other red blood cell sedimenting agents disclosed above. Insofar as the ratio of HES solution to the red blood cells is concerned, the best results have been obtained by utilizing a hematocrit of approximately 30%. However, good results can be obtained by having the hematocrit vary from 25 to 40%.

Without further elaboration, the foregoing will so fully illustrate my invention, that others may, by applying current or future knowledge, readily adapt the same for use under various conditions of service.

What is claimed as the invention is:

1. A leukopheresis process comprising withdrawing a portion of blood from a human, separating the red and white cells from the plasma and platelets in the blood, mixing the packed red and white cells with a solution comprising a red blood cell sedimenting agent and an isotonic balanced salt solution, said red blood cell sedimenting agent being present in a range of 1½ to 6% by weight of said isotonic balanced salt solution, permitting the mixture of red blood cells, white blood cells, sedimenting agent and isotonic balanced salt solution to stand to allow the red blood cells to sediment spontaneously to the bottom of the container in which the mixture is placed, separating the red blood cells, separating the white cells from the solution for transfusion to a patient, and reinjecting the red cells into the human donor of white cells.

2. The process of claim 1 wherein said red blood cell sedimenting agent is selected from the group consisting of high molecular weight dextran, fibrinogen, polyvinylpyrrolidone and hydroxyethyl starch.

3. The process of claim 2 wherein said red blood cell sedimenting agent is hydroxyethyl starch.

4. The process of claim 1 wherein sufficient red blood cell sedimenting agent in isotonic balanced salt solution is added to create a hematocrit in the range of 25 to 40%.

5. The process of claim 4 wherein the hematocrit is approximately 30%.

6. The method of claim 5 wherein said red blood cell sedimenting agent is hydroxyethyl starch.

7. The process of claim 1 and further including the steps of separating most of the platelets from the withdrawn platelet rich plasma in order to create platelet poor plasma, mixing the platelet poor plasma with the sedimented red blood cells, and reinjecting the mixture of the sedimented red cells and the platelet poor plasma into the human.

8. The process of claim 1 wherein the white cells are separated from the hydroxyethyl starch in isotonic balanced salt solution by centrifuging the bag containing the white cells in the solution in order to compact the white cells and leave the solution as the supernatant, and withdrawing the supernatant from the bag.

9. The process of claim 1 wherein said process is carried out more than twice on said human in a given day.

10. The process of claim 1 wherein said red blood cell sedimenting agent is hyroxyethyl starch, and said hydroxyethyl starch is present in an amount of approximately 3% by weight of said isotonic balanced salt solution.

11. The process of claim 1 wherein said red blood cells, white blood cells, sedimenting agent and isotonic balanced salt solution are permitted to stand in a platic bag for sedimentation, said plastic bag having a width of at least 4¾ inches (12.1cm).

12. The process of claim 11 wherein said plastic bag has a width of approximately 10½ inches (26.7cm).

13. The process of claim 1 wherein said red and white cells are separated from said plasma and platelets by centrifugation.

14. The process of claim 1 wherein said isotonic balanced salt solution comprises Normal Saline.

15. The process of claim 1 wherein the mixture consists essentially of red blood cells, white blood cells, hydroxyethyl starch and Normal Saline.

16. The process of claim 1 wherein said red blood cells are separated, after sedimentation, by gravity.

17. A process for harvesting granulocytes from portions of whole blood comprising centrifuging the blood to separate and remove the plasma and platelets, and to pack together the red cells and the white cells, suspending and packed red and white cells in a solution consisting essentially of hydroxyethyl starch in Normal Saline, said hydroxyethyl starch being present in the range of 1½ to 6% by weight of said Normal Saline, permitting the mixture of the red cells, white cells, hydroxyethyl starch and Normal Saline to stand until the red cells sediment spontaneously to the bottom of the container in which the mixture is placed, separating the red cells from the supernatant solution of HES, Normal Saline and white cells, concentrating the white cells by centrifuging the supernatant, and separating the white cells from the hydroxyethyl starch - Normal Saline solution.

* * * * *